(12) United States Patent
Tanaka

(10) Patent No.: US 11,350,583 B2
(45) Date of Patent: Jun. 7, 2022

(54) METHOD FOR ENHANCING PLANT CHARACTERISTICS AND METHOD FOR PRODUCING SEEDLESS FRUIT

(71) Applicant: Setsuzo Tanaka, Okayama (JP)

(72) Inventor: Setsuzo Tanaka, Okayama (JP)

( * ) Notice: Subject to any disclaimer, the term of this patent is extended or adjusted under 35 U.S.C. 154(b) by 48 days.

(21) Appl. No.: 16/608,698

(22) PCT Filed: Apr. 27, 2018

(86) PCT No.: PCT/JP2018/017206
§ 371 (c)(1),
(2) Date: Oct. 25, 2019

(87) PCT Pub. No.: WO2018/199293
PCT Pub. Date: Nov. 1, 2018

(65) Prior Publication Data
US 2021/0112741 A1    Apr. 22, 2021

(30) Foreign Application Priority Data

Apr. 27, 2017 (JP) .............................. JP2017-088327
Apr. 27, 2018 (JP) .............................. JP2018-086221

(51) Int. Cl.
| | | |
|---|---|---|
| A01H 5/08 | (2018.01) | |
| A01H 3/00 | (2006.01) | |
| A01G 2/30 | (2018.01) | |
| C12Q 1/6895 | (2018.01) | |

(52) U.S. Cl.
CPC ............... *A01H 5/08* (2013.01); *A01G 2/30* (2018.02); *A01H 3/00* (2013.01); *C12Q 1/6895* (2013.01)

(58) Field of Classification Search
None
See application file for complete search history.

(56) References Cited

U.S. PATENT DOCUMENTS

| | | | |
|---|---|---|---|
| 5,965,438 A | 10/1999 | Kadkade et al. | |
| 6,114,284 A | 9/2000 | Fujisawa et al. | |
| 2003/0182066 A1 | 9/2003 | Konishi | |
| 2003/0233681 A1 | 12/2003 | Zhu et al. | |
| 2010/0107473 A1 | 5/2010 | Zhang et al. | |

FOREIGN PATENT DOCUMENTS

| | | | | |
|---|---|---|---|---|
| CN | 106376341 A | * | 2/2017 | |
| EP | 830059 A2 | | 3/1998 | |
| EP | 1313055 A1 | | 5/2003 | |
| EP | 1496737 A2 | | 1/2005 | |
| JP | 11-507380 A | | 6/1999 | |
| JP | 2005-523719 A | | 8/2005 | |
| JP | 2006025632 A | | 2/2006 | |
| JP | 2007-308434 A | | 11/2007 | |
| JP | 2010-522562 A | | 7/2010 | |
| JP | 2016-21929 A | | 2/2016 | |
| JP | 2016182094 A | | 10/2016 | |
| JP | 6300215 B1 | | 3/2018 | |
| KR | 20070002208 A | | 1/2007 | |
| KR | 1020050057611 | * | 4/2007 | ............... A01H 4/00 |
| WO | 96/39812 A2 | | 12/1996 | |
| WO | 02/01477 A1 | | 1/2002 | |
| WO | 03/093411 A2 | | 11/2003 | |

OTHER PUBLICATIONS

P. Chouard, Vernalization and its Relations to Dormancy, Annual Reviews Plant Physiology, 1960, 11: 191-238 (Year: 1960).*
Dionne, Freezing Tolerance and Carbohydrate Changes during Cold Acclimation of Green-Type Annual Bluegrass (*Poa annua* L.) Ecotypes, Crop Sci. 41:443-451 (2001) (Year: 2001).*
North Dakota Monthly Climate Summary, Nov. 2015, https://www.ndsu.edu/fileadmin/ndsco/ndsco/summary/2015/11Nov2015.pdf (Year: 2015).*
https://www.ndsu.edu/fileadmin/ndsco/ndsco/summary/2015/11Nov2015.pdf and in further view of the North Dakota Monthly Climate Summary, Dec. 2015 (Year: 2015).*
Iordachescu, Trehalose Biosynthesis in Response to Abiotic Stress, Journal of Integrative Plant Biology, Oct. 10, 2008 (Year: 2008).*
Korner, Coldest places on earth with angiosperm plant life, Alp Botany, 2011, 121:11-22 (Year: 2011).*
International Search Report from PCT/JP2018/017206 dated Aug. 7, 2018 (3 pages).
Tanaka, Setsuzo, "Freeze-thaw awakening technique for seed (No. 1): Lowering temperature slowly and freezing", Modern agriculture, vol. 96, No. 3, Mar. 1, 2017, pp. 334-337, 334, 335, 336.
Tanaka, Setsuzo, "Freeze-thaw awakening technique for seed (No. 1): Raising memory of low-temperature resistance of crops using extremely low temperature", Modern agriculture, vol. 96, No. 1, Jan. 1, 2017, pp. 336-339, 33 9.
Tanaka, Setsuzo, "Papaya-banana, which is strong against low temperature and grows fast, was made", Modern agriculture, vol. 96, No. 2, Feb. 1, 2017, pp. 318-322.
Agritech Summit, URL:https://www.agsum.jp/news/005, paragraph [0005], non-official translation (Attention! Agricultural pioneers challenging harvest) , Feb. 18, 2017.
Yamada, Yasuaki, "Nikkei new and senior business-era project" Jul. 3, 2017], <URL:https://mbasic.facebook.com/nikkeiseniorproject?v=timeline_loading_div_1401605999_0_36_&timeend=1401605999&timestart=O&tm=AQDe6aksS1VcUNw6.
Tanaka, Setsuzo, et al., Monthly Columbus special brand, Monthly Columbus February issue, Toho Press, Jan. 27, 2016, pp. 19-21.

(Continued)

*Primary Examiner* — Matthew R Keogh
*Assistant Examiner* — Brian James Sullivan
(74) *Attorney, Agent, or Firm* — Calfee Halter & Griswold LLP

(57) ABSTRACT

To provide a novel technique for enhancing characteristics of a plant without using a gene recombination technique. A plant is treated with a freezing step of freezing a plant tissue, a thawing step of thawing the frozen plant tissue, and a generating step of generating a plant from the thawed plant tissue.

14 Claims, 11 Drawing Sheets

(56) References Cited

OTHER PUBLICATIONS

The Nikkei, the day when Japan becomes banana exporting country, The Nikkei electronic edition, <URL:https://www.nikkei.com/article/DGXMZ09868610U6A121C100 0000/>, Nov. 25, 2016.

Suzuki, Ryo, Nikkei senior staff writer, How recreating the ice age could solve food shortages, Nikkei Asian Review [online], <URL:https://www.nikkei.com/Business/How-recreating-the-ice-age-could-solve-food-shortages, Nov. 28, 2016.

Suzuki, Ryo, Nikkei senior staff writer, Growing bananas in the cold, Nikkei Asian Review [online], <URL:https://www.nikkei.com/Business/Growing-bananas-in-the-cold, Dec. 8, 2016.

Nakamura, Satoshi et al., "Freshness keeping effect of the disaccharide trehalose", Proceedings of the Annual Conference of the Japan Society of Waste Management Experts, vol. 9, No. 1, 1998, pp. 263-265.

Suzuki, Kunihiko, From one of origin names, papaya contains ingredient for assisting protein degradation, Table of stories, URL:http://www.zennokyo.co.jp/table/table_042.html, No. 171, Feb. 2012.

Momotaro Papaya Laboratory Inc. news, academic report, [online], Nov. 2016, <URL:http://www.mopalab.com/>.

Naoki, 7J=I 27 S/?/??—Yfc?, Cropnet, [online], Jul. 30, 2016, [search date Jul. 18, 2018], <URL:https://www.cropnet.p/page/182072>, entire text, non-official translation (Papaya record on Jul. 27).

ZventRegist, (Event-report) Agro-innovation 2015, (online), Nov. 18, 2015, EventRegist blog, (Jul. 13, 2017 search), URL:http://info.eventregist.com/weblog/report-agro-innovation-2015.

The dream day, which is Japan uses the fallow field as "the world's largest banana production area" (2/2), Jan. 10, 2017, Rakuten blogs, Jan. 10, 2017, Rakuten blogs URL:https://plaza.rakuten.co.jp/rakumeitei/diary/20170110/.

Agricultural Corporation, D & T Garden, Mongee Banana made in Okayama, (online),Jul. 13, (2017 search) URL:https://www.dt / farm.com/blank.

Takagi, H. et al., "Recent developments in cryopreservation of shoot apices of tropical species", International Agricultural Research Trails, 2000, No. 8, pp. 178-193.

Panis, B. et al., "Cryopreservation of banana (*Musa* spp.) meristem cultures after preculture on sucrose", Plant Sci., 1996, vol. 121, No. 1, p. 95-106.

Agricultural Corporation, D & T Garden, Mongee Banana made in Okayama, (online),(Jul. 13, 2017 search) URL:http://mongeebanana.com /.

Office Action dated 8 Aug. 8, 2017corresponding Japanese patent application No. 2017-088327.

English translation of Written Opinion for International Application No. PCT/JP2018/017206 dated Aug. 7, 2018.

\* cited by examiner

30 DAYS AFTER GERMINATION

UNTREATED  FREEZING AND THAWING TREATED

45 DAYS AFTER GERMINATION

UNTREATED     FREEZING AND THAWING TREATED

60 DAYS AFTER GERMINATION

UNTREATED   FREEZING AND THAWING TREATED

THREE MONTHS AFTER GERMINATION

UNTREATED     FREEZING AND THAWING TREATED

LEFT: BUD OF NORMAL PAPAYA
RIGHT: BUD OF PAPAYA, BUDDED IN THE COURSE OF SECOND GROWING STEP

TOP: CROSS SECTION OF BUD OF PAPAYA, BUDDED IN THE COURSE OF SECOND GROWING STEP
BOTTOM: CROSS SECTION OF BUD OF NORMAL PAPAYA

FREEZING AND  UNTREATED
THAWING TREATED

METHOD FOR ENHANCING PLANT CHARACTERISTICS AND METHOD FOR PRODUCING SEEDLESS FRUIT

CROSS-REFERENCE TO RELATED APPLICATIONS

This application is a 371 of PCT Application No. PCT/JP2018/017206 filed on Apr. 27, 2018, which claims priority to Japanese Application No. 2017-088327 filed on Apr. 27, 2017, and Japanese Application No. 2018-086221 filed on Apr. 27, 2018, the contents of which are hereby incorporated by reference as if recited in their entirety.

TECHNICAL FIELD

The present invention relates to a method for enhancing characteristics of a plant without using gene manipulation.

Further, the present invention relates to a technique for obtaining a seedless fruit without using gene manipulation or chemical treatment.

BACKGROUND ART

Since ancient times, human beings have produced a plant having advantageous properties by a breeding technique. The conventional breeding method requires a long time to fix the certain characteristics, however, with the advent of a generation acceleration technique, the time required for fixing the certain characteristics can be shortened. However, even with the generation acceleration technique, there has been a problem that it takes several years to fix the certain characteristics. Therefore, biotechnology such as anther culture that does not require any fixing work has been developed.

Further, a gene recombination technique is known as a method for producing a plant having advantageous characteristics. By the gene recombination technique, herbicide-tolerant crops, pest-resistant crops, disease-resistant crops, and crops with increased preservation have been produced.

On the other hand, a method has been proposed for inducing mutation and enhancing characteristics of a plant by performing a certain treatment. For example, in Patent Literature 1, a breeding method for imparting cold tolerance, including a step of performing gamma irradiation and chromosome doubling treatment has been disclosed.

Further, a method for controlling characteristics of a plant without changing the gene sequence has been devised. For example, in Patent Literature 2, a method for controlling the flowering time in the next generation of a plant by applying a stress treatment of salt stress, poor sunshine stress, strong light stress, drought stress, over-humidity stress, high-temperature stress, low-temperature stress, nutrient stress, heavy metal stress, disease stress, oxygen deficiency stress, ozone stress, $CO_2$ stress, strong wind stress, or the like due to the cultivation environment in the vegetative growth time of a plant has been disclosed.

By the way, most of the areas in Japan belong to the temperate zone, and Hokkaido and Tohoku region belong to the subarctic zone (cool-temperate zone). Therefore, crops that are not suitable for the cultivation in a climate in Japan, such as those cultivated in from the subtropical zone area to the tropical zone area, are in a situation of being dependent on the import.

Further, the expression "fruit" is generally referred to as a fruit having a structure containing seeds inside thereof in angiosperms. Therefore, normally, seeds are contained in a fruit, and it is required to remove the seeds when the fruit is eaten by humans because the seeds cannot be eaten by humans. However, the work of removing the seeds is complicated.

In view of such a problem, a method for producing a fruit with no seeds (seedless fruit) has been devised. As the typical method for obtaining a seedless fruit (anucleated), a gibberellin treatment method can be mentioned (Patent Literature 3).

Further, as in the case of the banana that has been generally distributed, production increase by a method in which a strain having a property of bearing a fruit with no seeds by mutation is multiplied by division has also been performed.

Depending on the kind of a plant, no pollination occurs, and there are some cases where a plant naturally bears a seedless fruit.

A *papaya* species, which has male trees and female trees, is an example of these cases, and if the pollination does not occur, parthenogenesis may occur. However, the efficiency is extremely low (around 5 to 10%).

Note that in *papaya* that is a species having male and female trees, a male flower and a female flower alternately come out and the self-pollination occurs, and therefore, the parthenogenesis hardly occurs.

Further, a *papaya* species obtained by breed improvement, in which parthenogenesis occurs, is known (Variety registration No. 16161).

CITATION LIST

Patent Literature

Patent Literature 1: JP 2006-25632 A
Patent Literature 2: JP 2016-182094 A
Patent Literature 3: Re-publication of PCT International Publication No. 97/031536

SUMMARY OF INVENTION

Technical Problem

As described above, most of the crops that are cultivated in the subtropical zone and the tropical zone are not suitable for cultivation in the temperate zone and the arctic zone, which requires them to be imported to the temperate zone and the arctic zone. However, as to the imported crops, there are some cases where a large amount of agricultural chemicals is used in order to realize the large-scale cultivation, or a chemical treatment such as fumigation treatment is performed for the importation, and many of the cases are harmful to the human body. Further, the imported crops to which such a chemical treatment has not been performed are expensive, and often not readily available.

In view of such a situation, a technique in which crops being cultivated in from the subtropical zone area to the tropical zone area can be cultivated in from the temperate zone to the arctic zone has been desired.

On the other hand, there are many cases where several years are required from the sowing to the harvesting depending on the plant species, and there may be a problem in the return on the investment for the cultivation of such a plant species.

In view of such a problem, a technique for accelerating the growth rate of a plant has been desired.

As described above, a technique for enhancing the growth rate and cold tolerance of a plant has been desired. There is a problem that it takes a long time to achieve the adoption of a breeding technique as the solution means. Further, the problem with an anther culture technique is that there is difficulty in the culture between plant species. In addition, with respect to a gene recombination technique, there is a problem of contamination in the gene pool, and in the method for inducing mutation, there is a problem that the degree of uncertainty in achieving the objective is high.

Further, a technique for enhancing the growth rate and environmental adaptation characteristics of a plant without changing the gene sequence has not been known.

In view of such a problem, the first problem to be solved by the present invention is to provide a novel technique for enhancing characteristics of a plant without using gene recombination.

Further, as described above, in a case where pollination is not performed, although the parthenogenesis can occur in papaya, the efficiency is extremely poor.

As the method for obtaining a papaya that bears a seedless fruit, breed improvement can be mentioned, however, it takes an extremely long period of time, and further the certainty is low.

On the other hand, there is a method of performing a chemical treatment such as gibberellin treatment, however, the method is not preferred because there is a problem of residual chemical substances or the like.

In view of such a problem, the second problem to be solved by the present invention is to provide a novel technique for obtaining a seedless fruit of papaya.

Solution to Problem

The present invention to solve the above-described first problem is a method for enhancing characteristics of a plant, including: a freezing step of freezing a plant tissue; a thawing step of thawing the frozen plant tissue; and a step of generating a plant from the thawed plant tissue.

According to the characteristic enhancement method of the present invention, in particular, the growth characteristics and/or cold tolerance of a plant can be enhanced.

Further, in a preferred mode of the present invention, the lowest temperature during freezing in the freezing step is −20° C. or less.

By setting the lowest temperature during freezing to −20° C. or less, the characteristics of a plant can be further enhanced.

In a preferred mode of the present invention, in the freezing step, the plant tissue is frozen while decreasing the temperature at a rate of 0.5° C./day or less.

By slowly decreasing the temperature in this way, the survival rate of the plant tissue after the thawing step can be improved, and the efficiency of the method according to the present invention can be improved.

In a preferred mode of the present invention, the period of the freezing step is 180 days or more.

By freezing the plant tissue over the above period, the effect of enhancing characteristics of a plant can be improved.

In a preferred mode of the present invention, in the freezing step, the plant tissue is frozen in a state of being immersed in an aqueous saccharide solution.

By setting the mode in such an embodiment, the survival rate of the plant tissue after the thawing step can be improved, and the efficiency of the method according to the present invention can be improved.

In a preferred mode of the present invention, the saccharides are trehalose.

By using trehalose, the survival rate of the plant tissue after the thawing step can be further improved.

The present invention to solve the second problem is a method for producing a seedless fruit of a plant belonging to the Caricaceae, characterized by including: a freezing step of freezing a plant tissue of a plant belonging to the Caricaceae; a thawing step of thawing the frozen plant tissue; a generating step of generating a plant from the thawed plant tissue, and a first growing step of growing the plant obtained by the generating step.

According to the production method of the present invention, a seedless fruit of a plant belonging to the Caricaceae can be obtained with high efficiency in a shorter period of time than that of breed improvement and without performing a chemical treatment such as gibberellin treatment.

In a preferred mode of the present invention, the first growing step is performed under an environment without pollination by a living organism. Since the pollination by an insect or the like does not occur, a seedless fruit can be obtained with extremely high efficiency.

In a preferred mode of the present invention, a culturing step of collecting a plant tissue of the plant grown by the first growing step and culturing the plant tissue; and a second growing step of growing the plant obtained by the culturing step are included.

The plant obtained by the first growing step also bears a seedless fruit, and the plant obtained by the second growing step through the culturing step has a unique property with which ovarian enlargement is observed at the budding stage, and occurrence of a seedless fruit can be confirmed. Further, buds in each of which the occurrence of a seedless fruit has been confirmed account for around 90% of the total buds. That is, the seedless fruit can be obtained with extremely high efficiency.

In a preferred mode of the present invention, the second growing step is open-field cultivation.

The plant obtained by the second growing step bears a seedless fruit with high efficiency even in open-field cultivation in which pollination by an insect normally may occur.

In a preferred mode of the present invention, a sorting step of observing a bud occurred in the course of the second growing step, and removing a bud in which the occurrence of a fruit has not been confirmed is included.

By removing the bud in which the occurrence of a fruit has not been confirmed in the sorting step, and leaving only the bud in which the occurrence of a fruit has been confirmed at the budding stage, fruits to be borne can be all made into seedless fruits.

The present invention also relates to a seedless fruit produced by the production method described above. Such a seedless fruit is different from a fruit that has been made seedless by chemicals such as gibberellin, and can be eaten at ease without worrying about residual substances.

Further, the present invention also relates to a plant bearing a seedless fruit obtained by the first growing step in the method for producing the seedless fruit described above. Such a plant bears a seedless fruit with high efficiency.

Further, the present invention also relates to a plant bearing a seedless fruit obtained by the second growing step in the method for producing the seedless fruit described above. Such a plant has a unique property with which ovarian enlargement is observed at the budding stage, and occurrence of a seedless fruit can be confirmed, as described above.

Further, by using the method described above, the present invention also relates to a plant in which the characteristics are enhanced, a plant tissue used as a scion for grafting, obtained from the plant, a plant obtained by grafting the plant tissue as a scion, and a plant tissue (except for a seed) obtained from each of the plants, and capable of generating a plant individual independent of the plant.

Further, the present invention also relates to a method for searching a gene for enhancing characteristics of a plant, characterized by including: a step of treating a plant by the method described above; and a step of identifying an RNA showing a higher expression level in the plant that has been subjected to the treatment as compared with an expression level in a plant that has not been subjected to the treatment.

Further, the present invention also relates to a method for screening a factor for enhancing characteristics of a plant, characterized by including screening a test substance as a factor for enhancing characteristics of a plant when an expression level of an RNA in a plant to which the test substance has applied is higher than an expression level of an RNA in a plant to which the test substance has not applied, by using as an indicator an RNA showing a higher expression level in a plant that has been subjected to the treatment described above as compared with an expression level in a plant that has not been subjected to the treatment.

According to the present invention, a factor for enhancing characteristics of a plant can be easily screened.

Advantageous Effects of Invention

According to the present invention to solve the first problem, a plant of which the characteristics have been enhanced can be obtained without using a breeding method over several years or a gene recombination method. In particular, according to the present invention, the growth characteristics and/or cold tolerance of a plant can be enhanced.

According to the present invention to solve the second problem, a seedless fruit of a plant belonging to the Caricaceae can be obtained with high efficiency.

DESCRIPTION OF EMBODIMENTS

[Characteristic Enhancement Method]

Figure 1:
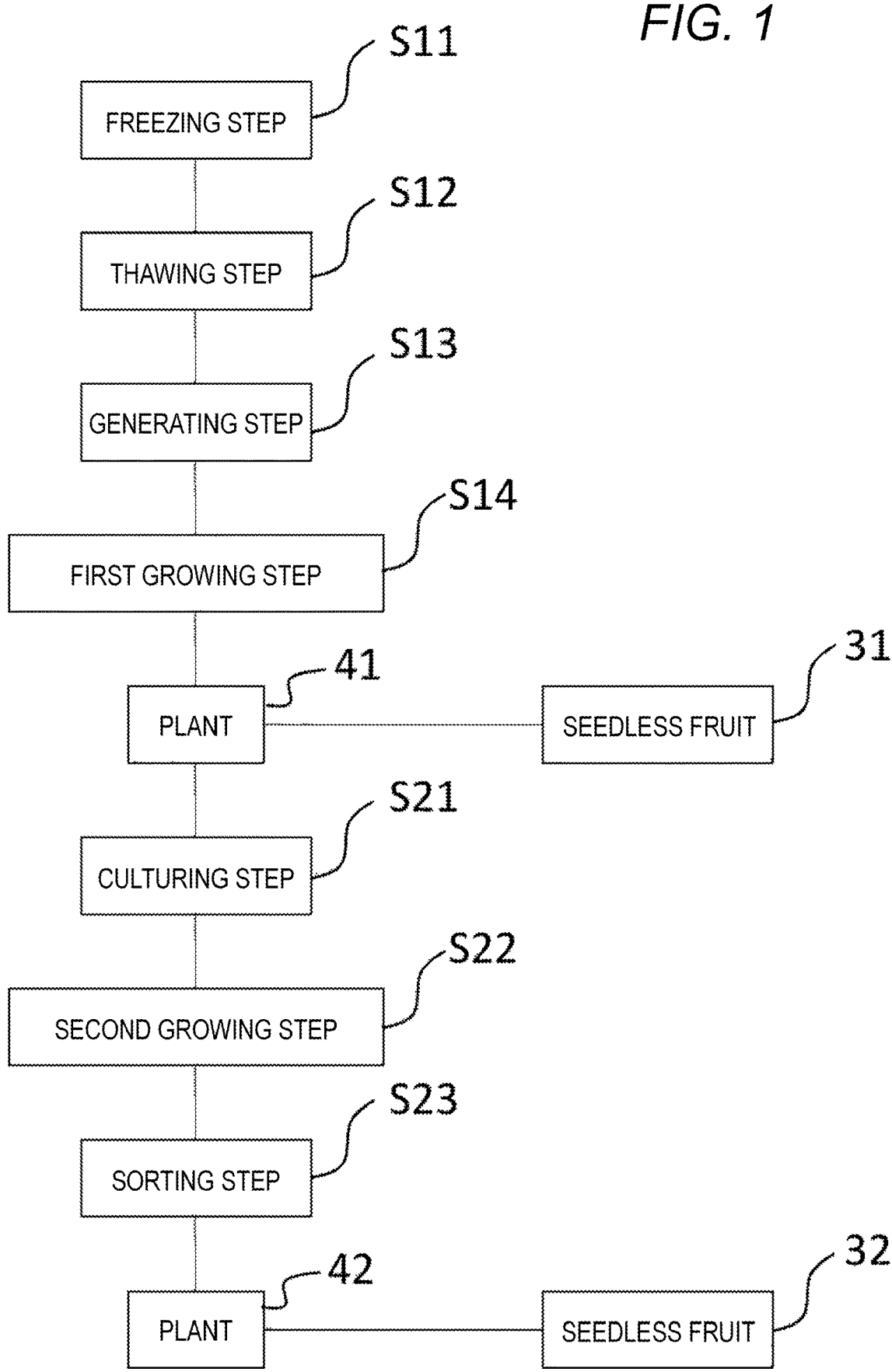
FIG. 1 is a scheme of a method for producing a seedless fruit.
Figure 2:
FIG. 2 is a photograph 30 days after germination of a *papaya* to which freezing and thawing treatment has been performed and a *papaya* to which the freezing and thawing treatment has not been performed.
Figure 3:
FIG. 3 is a photograph 45 days after germination of a *papaya* to which freezing and thawing treatment has been performed and a *papaya* to which the freezing and thawing treatment has not been performed.
Figure 4:
FIG. 4 is a photograph 60 days after germination of a *papaya* to which freezing and thawing treatment has been performed and a *papaya* to which the freezing and thawing treatment has not been performed.
Figure 5:
FIG. 5 is a photograph three months after germination of a *papaya* to which freezing and thawing treatment has been performed and a *papaya* to which the freezing and thawing treatment has not been performed.

The characteristic enhancement method according to the present invention can be applied to all of plant species without particular limitation, and application of the method to a plant belonging to, for example, the Caricaceae, the Bromeliaceae, the Musaceae, the Cucurbitaceae, the Myrtaceae, the Oxalidaceae, the Moraceae, the Malvaceae, the Rubiaceae, the Laureaceae, the Passifloraceae, the Sapindaceae, the Clusiaceae, the Ebenaceae, the Rutaceae, the Annonaceae, the Arecaceae, the Cactaceae, or the Rosaceae can be mentioned.

More specifically, application to a plant belonging to the *Carica*, the *Ananas*, the Musa, the Siraitia, the *Psidium*, the Averrhoa, the *Ficus*, the *Theobroma*, the *Coffea*, the *Cinnamomum*, the *Passiflora*, the Litchi, the Garcinia, the *Diospyros*, the Casimiroa, the Annona, the Phoenix, the Hylocereus, or the *Cerasus*, or the like can be mentioned.

The characteristic enhancement method according to the present invention includes a freezing step of freezing a plant tissue.

As the plant tissue subjected to the freezing step, a plant tissue that is obtained from a plant and can generate a plant individual independent of the plant can be preferably mentioned.

Since a plant is totipotent, any part of a plant corresponds to a "plant tissue that is obtained from a plant and can generate a plant individual independent of the plant", and as the part, specifically, a seed, a root, a sprout, a stem, a leaf, a petal, or the like of a plant can be mentioned, and preferably a seed, a root, or a sprout can be mentioned.

When the plant tissue is subjected to a freezing step, such a tissue may be frozen as it is, or a part of the tissue may be excised and frozen in a form of a section.

In the freezing step, it is preferred to freeze the plant tissue in a state of being immersed in a liquid. As a liquid to immerse the plant tissue, a cryoprotective agent including an aqueous solution of dimethyl sulfoxide (DMSO), glycerin, ethylene glycol, saccharides, or the like is preferably used. Among them, it is preferred to use an aqueous saccharide solution, or in particular, an aqueous trehalose solution.

The upper limit of the lowest temperature during freezing in the freezing step is preferably −20° C. or less, more preferably −30° C. or less, furthermore preferably −40° C. or less, still more preferably −50° C. or less, and still furthermore preferably −55° C. or less.

Further, the lower limit of the lowest temperature during freezing is preferably −200° C. or more, more preferably −150° C. or more, furthermore preferably −100° C. or more, still more preferably −80° C. or more, still furthermore preferably −70° C. or more, and even still more preferably −65° C. or more.

In the freezing step, it is preferred to slowly decrease the temperature rather than rapidly decrease the temperature to the lowest temperature during freezing. From the viewpoint of the survival rate after thawing, the rate of temperature decrease is preferably 0.8° C./day or less, more preferably 0.6° C./day or less, furthermore preferably 0.5° C./day or less, still more preferably 0.3° C./day or less, still furthermore preferably 0.2° C./day, and even still more preferably 0.1° C./day.

In a case where the temperature is slowly decreased as described above, it is preferred to use a program freezer in the freezing step.

The lower limit of the period of the freezing step is preferably 100 days or more, more preferably 120 days or more, furthermore preferably 150 days or more, still more preferably 160 days or more, and still furthermore preferably 180 days or more.

In this regard, the expression "period of the freezing step" is referred to as a period of time from the time point when the temperature of a plant tissue is started to decrease until the time point when a thawing step is started.

The thawing method in the thawing step is not particularly limited. The plant tissue in the frozen state may be naturally thawed by leaving the plant tissue at room temperature, or the plant tissue in the frozen state may be thawed while rinsing the plant tissue under running water.

The characteristic enhancement method according to the present invention includes a generating step of generating a plant from the plant tissue thawed as described above.

In a case where the plant tissue subjected to the freezing step and the thawing step is a seed of a plant, the seed is sown in accordance with a conventional method, and a plant individual can be generated.

In a case where the plant tissue subjected to the freezing step and the thawing step is a plant part other than the seed, the plant part may be transferred to soil or a medium as it is to allow to germinate, or by finely chopping the plant tissue, subjecting the chopped plant tissue to cell culture in accordance with a conventional method, and performing callus induction, adventitious embryo induction, or adventitious shoot induction on the cultured chopped plant tissue, a plant individual can be generated.

In the plant generated through the freezing step, thawing step, and generating step described above, the characteristics are enhanced.

More specifically, the growth rate and cold tolerance of a plant can be remarkably enhanced according to the characteristic enhancement method of the present invention.

That is, even if the plant is a plant that can be cultivated only in from the tropical zone area to the subtropical zone area, by applying the characteristic enhancement method according to the present invention to the plant, the plant can be cultivated in from the temperate zone area to the arctic zone area.

By the way, new Panama disease, which is an infection of banana caused by *Fusarium oxysporum* f. sp. *cubense* being one kind of fungi as a pathogen, gives damage to the banana cultivation in Malaysia, the Philippines, Taiwan, and African countries, and in recent years, the damage to the banana cultivation has been spread also in China, Indonesia, Australia, Jordan, Mozambique, and Central American countries.

This mold fungus causes damages of infection in from a subtropical zone area to a tropical zone area, however, does not spread in from the temperate zone area to the arctic zone area because the temperature deviates from the optimum temperature.

Therefore, if the cold tolerance of banana is enhanced by the characteristic enhancement method according to the present invention, and the banana with the enhanced cold tolerance is cultivated in from a temperate zone to an arctic zone, the banana can be supplied stably without being exposed to the threat of new Panama disease.

In addition, according to a preferred mode of the characteristic enhancement method of the present invention, environmental adaptation characteristics such as heat tolerance, a high altitude adaptation characteristic, and a low altitude adaptation characteristic can be enhanced. That is, according to the characteristic enhancement method of the present invention, even if the plant is a plant that can be cultivated only in from the temperate zone area to the arctic zone area, the plant can be made adaptable to the cultivation in from the tropical zone area to the subtropical zone area, and a plant that is cultivated in highlands can be made adaptable to the cultivation in lowlands, and vice versa.

Further, according to a preferred mode of the characteristic enhancement method of the present invention, the fertility, pest resistance, and root rot resistance of a plant can also be enhanced.

The characteristic enhancement method according to the present invention may include more preferably a screening step.

That is, in a case of using a seed as the plant tissue, multiple seeds are subjected to a freezing step, a thawing step, and a generating step, and each of the seeds is germinated and cultivated, and a strain having excellent characteristics may be screened among the resultant strains.

Further, in a case of using ones other than the seed as the plant tissue, a plant individual is generated from multiple buds, calli, adventitious embryos, or adventitious shoots, which have been generated after being subjected to a freezing step, a thawing step, and a generating step, and a strain having excellent characteristics may be screened among the resultant strains.

The next-generation plant obtained by a method other than sexual reproduction from the plant to which the characteristic enhancement method according to the present invention has been applied takes over the enhanced characteristics. Therefore, if a plant in which the characteristics have been enhanced by the characteristic enhancement method according to the present invention can be obtained, the progeny in the next and future generations generated from a plant tissue (child strain or the like) other than the seed, which is obtained from a plant and can generate a plant individual independent of the plant, also have the enhanced characteristics.

Further, even in a case where a plant to which the characteristic enhancement method according to the present invention has been applied is used as a scion for grafting, the progeny exhibit the enhanced characteristics.

In a plant that has been subjected to a treatment by the characteristic enhancement method according to the present invention, the level of the RNA expressed in a cell of the plant is significantly increased as compared with that of a plant that has not been subjected to the treatment. It can be said that this remarkable increase in the level of RNA is a factor for enhancing the characteristics. That is, it can be said that the gene encoding an RNA whose expression level increases in a plant cell by applying the characteristic enhancement method according to the present invention is a gene for enhancing the characteristics of the plant.

Therefore, by analyzing and identifying the RNA whose expression level increases in a plant cell by applying the characteristic enhancement method according to the present invention, a gene for enhancing the characteristics of the plant can be searched.

That is, the present invention also relates to a method for searching a gene for enhancing characteristics of a plant, including a step of treating a plant by the characteristic enhancement method described above, and a step of identifying an RNA showing a higher expression level in a plant that has been subjected to the treatment as compared with that in a plant that has not been subjected to the treatment.

The step of identifying the RNA in the searching method according to the present invention can be performed in the conventional method. For example, by transcriptome analysis such as microarray or RNA sequencing, the RNA showing a high expression level in a plant that has been subjected to the treatment by the characteristic enhancement method according to the present invention can be identified.

Further, as described above, since the RNA whose expression level increases in a plant to which the characteristic enhancement method according to the present invention has applied is a factor for enhancing the characteristics, if the RNA is used as an indicator, the factor for enhancing the characteristics of a plant can be screened.

That is, the present invention also relates to a method for screening a test substance as the factor for enhancing the characteristics of a plant when an expression level of the RNA in a plant to which the test substance has applied is higher than that of the RNA in a plant to which the test substance has not applied.

The expression level of the RNA, which is a factor for enhancing the characteristics of a plant, can be confirmed by a conventional method such as Northern blotting or real-time polymerase chain reaction (PCR).

[Method for Producing Seedless Fruit]

Hereinafter, an embodiment of the present invention will be described in detail with reference to FIG. 1.

The method for producing a seedless fruit according to the present invention can be applied to a plant belonging to the Caricaceae, such as the *Cylicomorpha*, the *Carica*, the *Horovitzia*, the *Jarilla*, the *Jacaratia*, and the *Vasconcellea*. Specifically, the method can be applied to a plant belonging to the *Carica*, and more specifically, to a *papaya* (*Carica papaya* L).

The method for producing a seedless fruit according to the present invention includes a freezing step S11 of freezing a plant tissue.

As the plant tissue to be subjected to the freezing step S11, a plant tissue that is obtained from a plant and can generate a plant individual independent of the plant can be preferably mentioned.

Since a plant is totipotent, any part of a plant corresponds to a "plant tissue that is obtained from a plant and can generate a plant individual independent of the plant", and as the part, specifically, a seed, a root, a sprout, a stem, a leaf, a petal, or the like of a plant can be mentioned, and preferably a seed, a root, or a sprout, and more preferably a seed can be mentioned.

When the plant tissue is subjected to a freezing step S11, such a tissue may be frozen as it is, or a part of the tissue may be excised and frozen in a form of a section.

In the freezing step S11, it is preferred to freeze the plant tissue in a state of being immersed in a liquid. As a liquid to immerse the plant tissue, a cryoprotective agent including an aqueous solution of dimethyl sulfoxide (DMSO), glycerin, ethylene glycol, saccharides, or the like is preferably used. Among them, it is preferred to use an aqueous saccharide solution, or in particular, an aqueous trehalose solution.

The upper limit of the lowest temperature during freezing in the freezing step S11 is preferably −20° C. or less, more preferably −30° C. or less, furthermore preferably −40° C. or less, still more preferably −50° C. or less, and still furthermore preferably −55° C. or less.

Further, the lower limit of the lowest temperature during freezing is preferably −200° C. or more, more preferably −150° C. or more, furthermore preferably −100° C. or more, still more preferably −80° C. or more, still furthermore preferably −70° C. or more, and even still more preferably −65° C. or more.

In the freezing step S11, it is preferred to slowly decrease the temperature rather than rapidly decrease the temperature to the lowest temperature during freezing. From the viewpoint of the survival rate after thawing, the rate of temperature decrease is preferably 0.8° C./day or less, more preferably 0.6° C./day or less, furthermore preferably 0.5° C./day or less, still more preferably 0.3° C./day or less, still furthermore preferably 0.2° C./day, and even still more preferably 0.1° C./day.

In a case where the temperature is slowly decreased as described above, it is preferred to use a program freezer in the freezing step S11.

The lower limit of the period of the freezing step S11 is preferably 100 days or more, more preferably 120 days or more, furthermore preferably 150 days or more, still more preferably 160 days or more, and still furthermore preferably 180 days or more.

In this regard, the expression "period of the freezing step S11" is referred to as a period of time from the time point when the temperature of a plant tissue is started to decrease until the time point when a thawing step S12 is started.

The thawing method in the thawing step S12 is not particularly limited. The plant tissue in the frozen state may be naturally thawed by leaving the plant tissue at room temperature, or the plant tissue in the frozen state may be thawed while rinsing the plant tissue under running water.

The method for producing a seedless fruit according to the present invention includes a generating step S13 of generating a plant from the plant tissue thawed as described above.

In a case where the plant tissue subjected to the freezing step S11 and the thawing step S12 is a seed of a plant, the seed is sown in accordance with a conventional method, and a plant individual can be generated.

In a case where the plant tissue subjected to the freezing step S11 and the thawing step S12 is a plant part other than the seed, the plant part may be transferred to soil or a medium as it is to allow to germinate, or by finely chopping the plant tissue, subjecting the chopped plant tissue to cell culture in accordance with a conventional method, and performing callus induction, adventitious embryo induction, or adventitious shoot induction on the cultured chopped plant tissue, a plant individual can be generated.

The plant individual generated by the generating step S13 is grown in a first growing step S14. The first growing step S14 may be performed by any method, and a known plant cultivation method such as open-field cultivation, greenhouse cultivation, or closed-door cultivation can be applied.

If natural pollination by an insect occurs, a plant 41 to be grown by the first growing step S14 bears a fruit containing seeds. Therefore, in the first growing step S14, in order to further improve the efficiency of parthenogenesis, it is preferred to perform the step by closed-door cultivation or the like under an environment without pollination by a living organism such as an insect.

In view of the optimum temperature in the cultivation of a plant belonging to the Caricaceae, the first growing step S14 may be performed in from the tropical zone area to the subtropical zone area, or in a room where the temperature is controlled so as to be equivalent to the climates in these areas.

In this regard, in the plant 41 that has gone through the freezing step S11, the thawing step S12, and the generating step S13, the cold tolerance is dramatically improved, and therefore, the plant 41 can also be cultivated in from the temperate zone area to the arctic zone area, where the temperature is lower than that in from the tropical zone area to the subtropical zone area, or in a room where the temperature is controlled so as to be equivalent to the climates in these areas.

If natural or artificial pollination is not performed, the plant 41 grown in the first growing step S14 bears a seedless fruit 31 with high efficiency.

In also a plant belonging to the Caricaceae, which has cultivated by an ordinary cultivate method, parthenogenesis occurs unless pollination is performed, however, the efficiency is extremely low. On the other hand, in the plant 41 grown in the first growing step S14, the parthenogenesis occurs with extremely high efficiency, and therefore, the plant 41 is particularly excellent in the productivity of a seedless fruit.

In a preferred embodiment of the present invention, a plant tissue of the plant grown by the first growing step S14 is collected, and cultured (culturing step S21). As the method for culturing a tissue, it is not particularly limited, and organ culture for culturing an organ such as a leaf, mericlone culture (shoot tip culture) for culturing a shoot apex, embryo culture for culturing an immature embryo, anther culture for culturing an anther, protoplast culture for culturing a protoplast, or the like can be mentioned.

Needless to say, the culturing step S21 is not required to wait until the plant 41 bears a fruit in the first growing step S14. Even if the plant is a plant 41 at any growth stage, the plant can be subjected to the culturing step S21.

A plant individual is newly generated by the culturing step S21, and then a second growing step S22 for growing the obtained plant is performed.

With respect to the conditions in the second growing step S22, the above-described content of the first growing step S14 can be applied. However, a plant 42 that has gone through the culturing step S21 has a unique property with which ovarian enlargement is observed at the budding stage, and occurrence of a seedless fruit can be confirmed. Further, buds in each of which the occurrence of a seedless fruit has been confirmed account for around 90% of the total buds. In this way, since buds in each of which the occurrence of parthenogenesis has been confirmed at the budding stage account for almost all the buds, there is no problem that the natural pollination by an insect is generated by performing open-field cultivation and the efficiency of parthenogenesis is decreased. Therefore, the second growing step S22 may be performed by open-field cultivation. It is extremely advantageous to perform the second growing step S22 by open-field cultivation also in terms of reduction in the production cost.

As described above, in the plant 42 that has gone through the culturing step S21, the parthenogenesis can be confirmed in a state of a bud. Therefore, it is preferred to perform a sorting step S23 of removing a bud in which occurrence of a fruit has not been confirmed (it is possible to bear a fruit having seeds by pollination). If the sorting step S23 is performed, the proportion of the seedless fruits 32 in the total fruits that have each borne a fruit can be improved. If all of the buds in each of which occurrence of a fruit has not been confirmed are removed by the sorting step S23, all of the fruits that have each borne a fruit can be made into seedless fruits 32.

As described above, the plants 41 and 42 each have a property of bearing a seedless fruit with high efficiency. The next-generation plant obtained by a method other than sexual reproduction from each of the plants 41 and 42 takes over the characteristic of parthenogenesis with high efficiency. Therefore, the progeny in the next and future generations generated from a plant tissue (child strain or the like) other than a seed, which is obtained from the plants 41 and 42 and can generate a plant individual independent of the plants, also have the characteristic of parthenogenesis with high efficiency.

Further, even in a case where the plants 41 and 42 are each used as a scion for grafting, the characteristic of parthenogenesis can be exhibited with high efficiency.

EXAMPLES

<Test Example 1> Enhancement of Characteristics and Production of Seedless Fruit of *Papaya*

A seed of *papaya* was left to stand in a program freezer and frozen in a state of being immersed in an aqueous trehalose solution (freezing step). The freezing was performed slowly over 180 days at a temperature decrease rate of 0.5° C./day so that the lowest temperature during freezing was −60° C.

The frozen seed of *papaya* was thawed while rinsing the frozen seed under running water (thawing step), and the thawed seed was sown and cultivated (generating step, first growing step). Further, the cultivation area is Okayama Prefecture in Japan.

In FIGS. 2 to 6, the results of observation over time of the growth of each of the seed that had been subjected to freezing and thawing treatment and the seed that had not been subjected to the freezing and thawing treatment are shown.

As shown in FIGS. 2 to 6, it was able to be confirmed that the growth rate of the *papaya* that had been subjected to the freezing and thawing treatment described above was significantly improved as compared with that of the *papaya* that had not been subjected to the freezing and thawing treatment. This result shows that the growth characteristics of a plant can be enhanced according to the characteristic enhancement method of the present invention.

Further, *papaya* is a plant that is native of from southern Mexico to the West Indies and is cultivated in tropical countries, and the *papaya* has a property of poor cold tolerance. However, the *papaya* that had been subjected to freezing and thawing treatment grew without having any problems as shown in FIGS. 2 to 6, in spite of the fact that the cultivation area was Okayama Prefecture in Japan belonging to the temperate zone. This result shows that the cold tolerance of a plant can be enhanced according to the characteristic enhancement method of the present invention.

Figure 6:
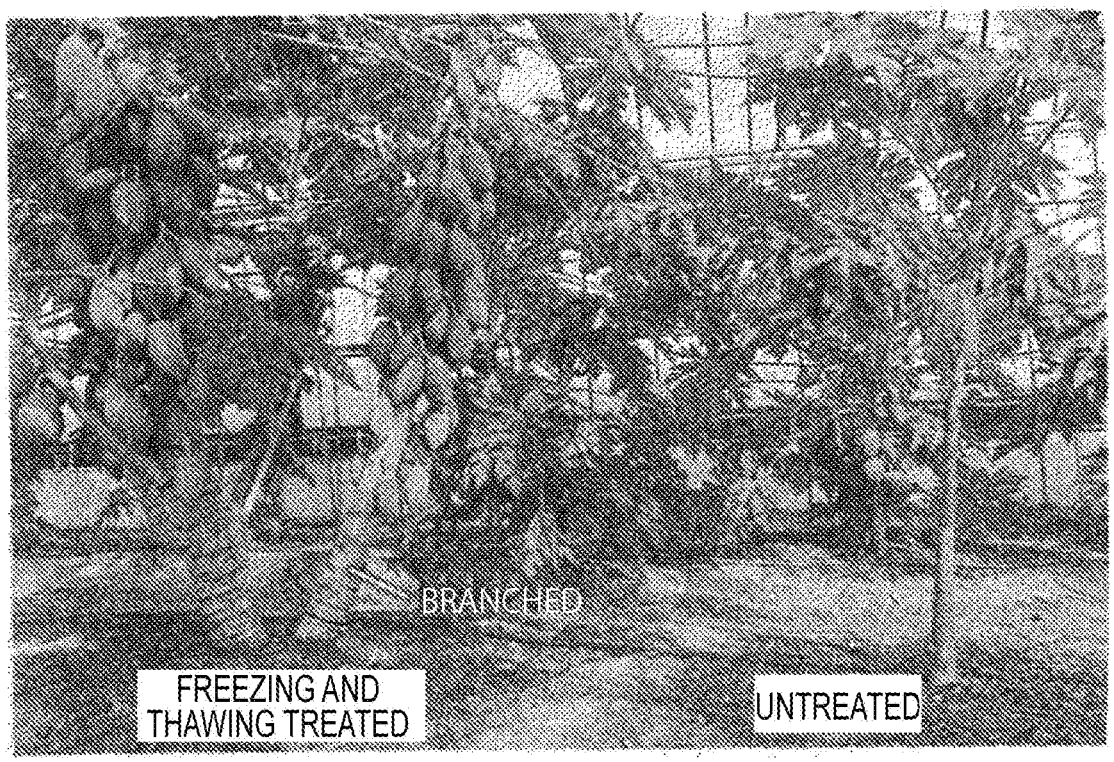
FIG. 6 is a photograph at harvest time of a *papaya* to which freezing and thawing treatment has been performed and a *papaya* to which the freezing and thawing treatment has not been performed.

In addition, as shown in FIG. 6, the *papaya* that had been subjected to the freezing and thawing treatment bore more fruits than those of the *papaya* that had not been subjected to the freezing and thawing treatment bore. This result shows that the fertility of a plant can be enhanced according to the characteristic enhancement method of the present invention.

In the present Test Example, although agricultural chemicals were not used, *papaya* was able to be cultivated without being damaged by disease and insect pests. Further, even in a case where the *papaya* to which the freezing and thawing treatment had been performed in a similar manner as in the present Test Examples was cultivated on a large scale without using any agricultural chemicals, the *papaya* was able to be cultivated without being damaged by disease and insect pests. This result shows that the pest resistance of a plant can be enhanced according to the characteristic enhancement method of the present invention.

Further, in the *papaya* that had been subjected to the freezing and thawing treatment, resistance to root rot was observed. This result shows that the root rot resistance of a plant can be enhanced according to the characteristic enhancement method of the present invention.

Borne fruits of *papaya* were harvested, and when the content of each of the fruits was checked, around 95% of the total fruits were seedless fruits.

When the results described above are summarized, it has been found that by subjecting a *papaya* to a freezing step, a thawing step, a generating step, and a first growing step, a seedless fruit of the *papaya* can be obtained with high efficiency. Further, the *papaya* cultivated by the present method was extremely excellent in the fertility. That is, it has been found that by the method according to the present invention, a seedless fruit can be obtained with extremely high productivity.

In addition, a *papaya* cultivated by the present method is excellent in the cold tolerance, the insect resistance, and the root rot resistance, and therefore, the first growing step can be performed even in the temperate zone, and agrochemical-free cultivation can also be performed.

<Test Example 2> Production of Seedless Fruit of Papaya (2)

A shoot apex of a *papaya* obtained by the freezing step, thawing step, generating step, and first growing step in Test Example 1 was collected, and the collected shoot apex was mericlone cultured (culturing step). A seedling of the *papaya* individual generated through the culturing step was subjected to open-field cultivation (second growing step).

Figure 7:
FIG. 7 is a comparison photograph of a bud of a normal *papaya* and a bud of a *papaya* that has borne a fruit in the course of the second growing step.
Figure 8:
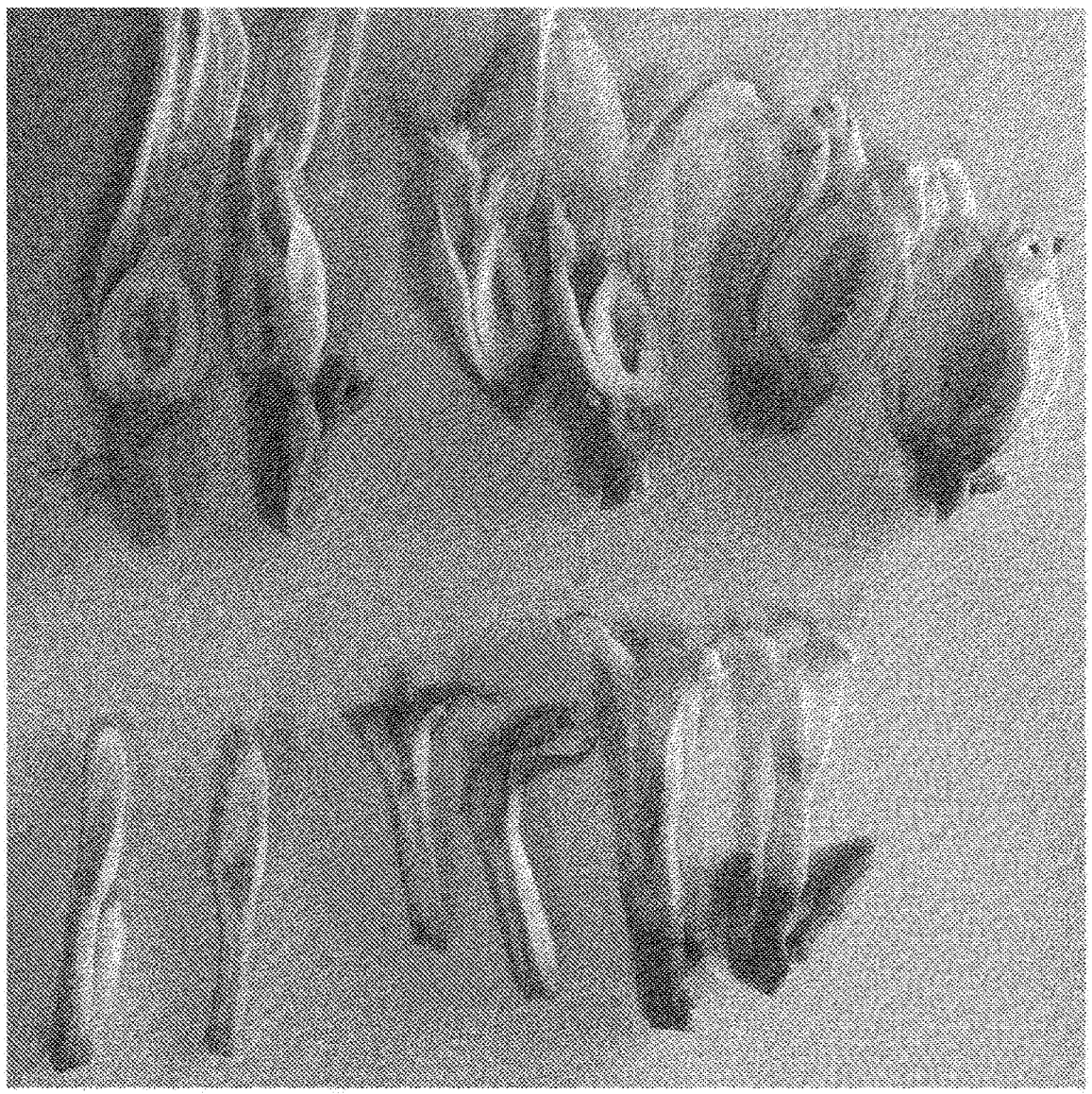
FIG. 8 is a comparison photograph of cross sections of buds of a normal *papaya* and a *papaya* that has borne a fruit in the course of the second growing step.

In FIGS. 7 and 8, comparison photographs of a bud budded in the course of the second growing step and a bud of a normal *papaya* are shown, and the difference between the buds is obvious at a glance. As shown in FIG. 7, in the bud budded in the course of the second growing step, ovarian enlargement was observed. Further, as shown in FIG. 8, it can be understood that the bud budded in the course of the second growing step has already borne a fruit when the cross section of the bud is observed. Since the fruit that has been borne at this budding stage is not pollinated, the fruit is naturally a seedless fruit.

The proportion of the buds in which parthenogenesis had been confirmed to the total buds that had budded in the course of the second growing step was around 90%.

A bud in which ovarian enlargement had not been confirmed (around 10%) as shown in FIG. 7 was sorted, and removed (sorting step). After the sorting step, eventually, all of the fruits obtained from the *papaya* that had grown in the second growing step were seedless fruits.

<Test Example 3> Characteristic Enhancement of Pineapple

Figure 9:
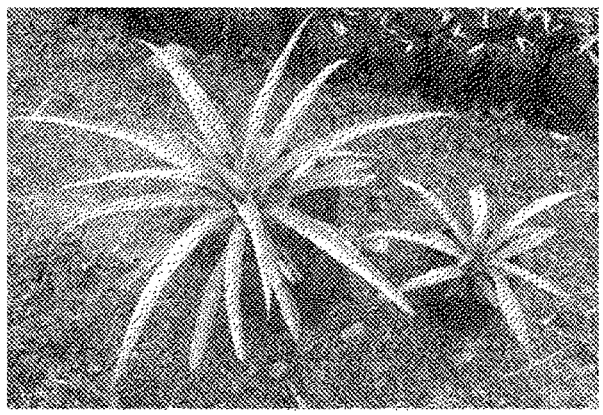
FIG. 9 is photographs showing the cultivated states observed over time of a pineapple to which freezing and thawing treatment has been performed and a pineapple to which the freezing and thawing treatment has not been performed. The photograph in the lowest part shows the pineapples one year after germination.
Figure 9:
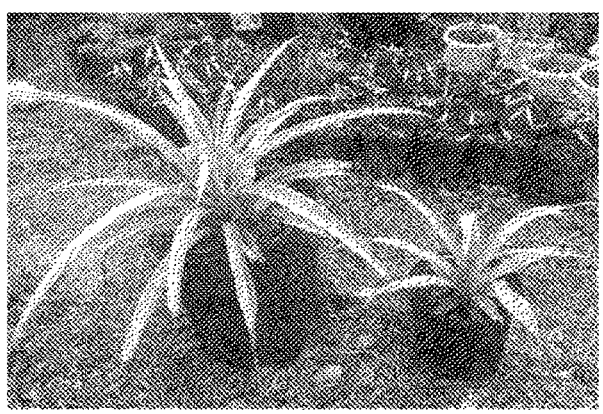
Figure 9:
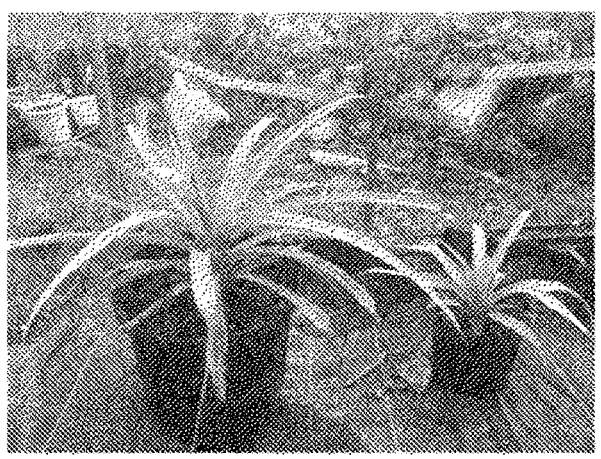

A seed of a pineapple was subjected to freezing and thawing treatment in a similar manner as in Test Example 1, and the treated seed was sown and cultivated. In FIG. 9, photographs are shown, which have recorded over time the growth of the pineapple that had been subjected to the freezing and thawing treatment and the growth of the pineapple that had not been subjected to the freezing and thawing treatment, seeds of both pineapples were sown and cultivated at the same time.

As shown in FIG. 9, as is the case with the *papaya* in Test Example 1, also in a pineapple, enhancement of the growth characteristics and cold tolerance by the freezing and thawing treatment was able to be confirmed.

<Test Example 4> Characteristic Enhancement of Banana (1)

A root of a child strain of a banana was sliced into rings, and each of the rings was frozen and thawed in a similar manner as in Test Example 1. The root of the child strain after the freezing and thawing was finely chopped, and this finely-chopped growth cell cluster was cultured on a medium and allowed to germinate. The seedling grown to some extent was transferred to soil and cultivated. Further, the cultivation was performed in Okayama Prefecture in Japan.

Figure 10:
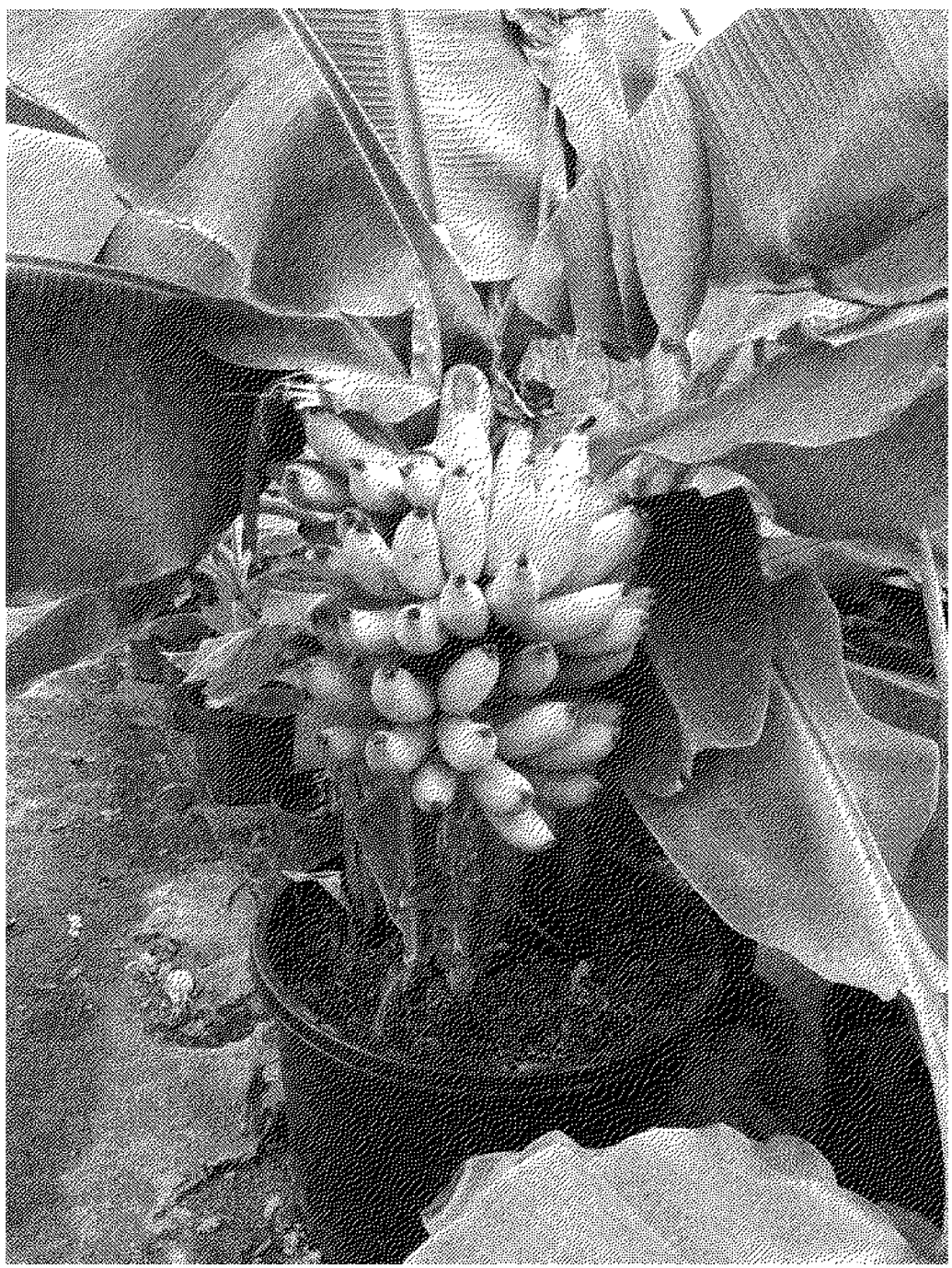
FIG. 10 is a photograph of a cultivated banana to which freezing and thawing treatment has been performed.

As a result, the seedling has grown to be in a state that the fruit can be harvested, in around 9 months after the seedling was planted (FIG. 10). In general, it takes at least one year for a banana to be in a state that the fruit can be harvested from the time when a seedling of the banana was planted, however, this result shows that the growth rate of the banana can be remarkably improved by the freezing and thawing treatment.

Further, as in the case of a *papaya*, a banana is also native of from the subtropical zone to the tropical zone, and in general, does not bear a fruit in the temperate zone, however, in the present Test Example, the banana was cultivated also in Okayama Prefecture in Japan belonging to the temperate zone, and the fruit was able to be harvested (FIG. 10).

This result shows that the cold tolerance of the banana can be enhanced by the freezing and thawing treatment.

<Test Example 5> Characteristic Enhancement of Banana (2)

A side bud generated from the plant foot of a banana was cut out, the leaves and root were cut off, and the side bud was processed to have a bamboo-shoot shape. The processed side bud was frozen and thawed in a similar manner as in Test Example 1. The side bud after the thawing was planted in a pot. After that, the stem rotted and disappeared, however, it was confirmed that a bud newly germinated. When this newly germinated bud was cultivated, a banana in which the growth rate and cold tolerance had been enhanced was able to be obtained in a similar manner as in Test Example 4.

<Test Example 6> Characteristic Enhancement of Coffee

Figure 11:
FIG. 11 is photographs of cultivated coffee trees to which freezing and thawing treatment has been performed.
Figure 11:

A seed of a coffee tree, which has been cultivated in Tainan city in Taiwan, was subjected to freezing and thawing treatment and germinated in a similar manner as in Test Example 1, and the germinated seed was cultivated in Okayama Prefecture in Japan (FIG. 11). As a result, in the coffee tree that had been subjected to the freezing and thawing treatment, acceleration at a growth rate of 3 to 40% was observed as compared with that of the same body of the coffee tree cultivated in Tainan city, which had not been subjected to the freezing and thawing treatment.

This result shows that the growth rate of the coffee tree can be improved by the freezing and thawing treatment.

Further, the grown was observed without having any problems in Okayama Prefecture in Japan where the temperature is lower than that in Tainan city in Taiwan, and therefore, it shows that the cold tolerance of the coffee tree can be improved by the freezing and thawing treatment.

<Test Example 7> Characteristic Enhancement of Other Plant Species

A seed of each of the plants listed below was subjected to freezing and thawing treatment in a similar manner as in Test Example 1, and a plant individual was generated from a plant tissue after the treatment, and cultivated.

The plants are listed as follows: Lo Han Kuo, guava, star fruit, fig, cacao, Ceylon cinnamon, passionfruit, litchi, mangosteen, black sapote, white sapote, spine sugar apple, date palm, red dragon fruit, and almond.

As a result, also in any one of the plant species listed above, enhancement of the growth characteristics and cold tolerance by the freezing and thawing treatment was able to be confirmed.

This result shows that the characteristic enhancement method according to the present invention is effective to all of the plant species.

<Test Example 8> Molecular Biological Analysis

*Papaya*, banana, passionfruit, and guava fruit, in each of which the characteristics had been enhanced by the freezing and thawing treatment in the above Test Example, were subjected to transcriptome analysis by using a plant that had not been subjected to the freezing and thawing treatment as a comparison object. As a result, it has been found that in any one of the plants, the expression level of mRNA is improved by around 32 to 38 times by being subjected to the freezing and thawing treatment.

This result shows that the expression of a gene for enhancing the growth characteristics and cold tolerance is remarkably improved by the freezing and thawing treatment.

That is, it is shown that by analyzing the mRNA improved by the freezing and thawing treatment, a gene for enhancing the characteristics of a plant, such as growth characteristics and cold tolerance can be identified.

Further, this result shows that by using the mRNA that is a transcription product of the above-described enhancing gene as an indicator, a factor for enhancing the characteristics of a plant, such as growth characteristics and cold tolerance can be screened.

INDUSTRIAL APPLICABILITY

The present invention can be applied to a production technique for crops.

Further, the present invention can be applied to production of a seedless fruit of *papaya*.

What is claimed is:

1. A method for enhancing characteristics of a plant, comprising:
    a freezing step of freezing a plant tissue;
    a thawing step of thawing the frozen plant tissue; and
    a generating step of generating a plant from the thawed plant tissue;
    wherein the method is a method for enhancing growth characteristics and/or cold tolerance of a plant, compared to plants that have not been subjected to the freezing and thawing steps,
    wherein a lowest temperature during freezing in the freezing step is −20° C. or less,
    wherein in the freezing step, the plant tissue is frozen while continuously decreasing the temperature at a rate of 0.8° C./day or less, day to day,
    wherein a period of the freezing step is 100 days or more.

2. The method for enhancing characteristics of a plant according to claim 1, wherein
    a lowest temperature during freezing in the freezing step is −55° C. or less.

3. The method for enhancing characteristics of a plant according to claim 1, wherein
    in the freezing step, the plant tissue is frozen while continuously decreasing the temperature at a rate of 0.5° C./day or less, day to day.

4. The method for enhancing characteristics of a plant according to claim 1, wherein
    a period of the freezing step is 180 days or more.

5. The method for enhancing characteristics of a plant according to claim 1, wherein
    in the freezing step, the plant tissue is frozen in a state of being immersed in an aqueous saccharide solution.

6. The method for enhancing characteristics of a plant according to claim 5, wherein
    the saccharides are trehalose.

7. A method for producing a seedless fruit of a plant belonging to the Caricaceae, comprising:
    applying the method for enhancing characteristics of a plant according to claim 1 to a plant belonging to the Caricaceae; and
    a first growing step of growing the plant obtained by the generating step.

8. The method for producing a seedless fruit according to claim 7, wherein
    the first growing step is performed under an environment without pollination by a living organism.

9. The method for producing a seedless fruit according to claim 7, comprising:
    a culturing step of collecting and culturing a plant tissue of the plant grown by the first growing step; and
    a second growing step of growing the plant obtained by the culturing step.

10. The method for producing a seedless fruit according to claim 9, wherein
    the second growing step is open-field cultivation.

11. The method for producing a seedless fruit according to claim 9, comprising:
    a sorting step of observing a bud generated in the course of the second growing step, and removing a bud in which a fruit has not been confirmed.

12. A method for searching a gene for enhancing characteristics of a plant, comprising:
    a step of treating a plant by the method according to claim 1; and
    a step of identifying an RNA showing a higher expression level in the plant subjected to the treatment as compared with an expression level in a plant not subjected to the treatment.

13. The method for enhancing characteristics of a plant according to claim 1, wherein in the generating step, the plant individual is generated by subjecting the plant tissue to cell culture and performing callus induction.

14. The method for enhancing characteristics of a plant according to claim 1, wherein the growth characteristics include a growth rate of the plant.

\* \* \* \* \*